United States Patent
Isaacson et al.

(10) Patent No.: US 11,666,736 B2
(45) Date of Patent: Jun. 6, 2023

(54) CATHETER ASSEMBLY

(71) Applicant: Becton, Dickinson and Company, Franklin Lakes, NJ (US)

(72) Inventors: Ray Isaacson, Layton, UT (US); Fidelin Willybiro, Park City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 634 days.

(21) Appl. No.: 16/673,294

(22) Filed: Nov. 4, 2019

(65) Prior Publication Data

US 2020/0061347 A1    Feb. 27, 2020

Related U.S. Application Data

(63) Continuation of application No. 15/664,827, filed on Jul. 31, 2017, now Pat. No. 10,500,375.

(51) Int. Cl.
*A61M 25/06* (2006.01)
*A61M 25/00* (2006.01)
*A61M 39/10* (2006.01)
*A61M 5/32* (2006.01)

(52) U.S. Cl.
CPC ...... *A61M 25/0618* (2013.01); *A61M 5/3273* (2013.01); *A61M 25/0097* (2013.01); *A61M 25/0606* (2013.01); *A61M 25/0631* (2013.01); *A61M 39/10* (2013.01); *A61M 2039/1077* (2013.01)

(58) Field of Classification Search
CPC ...... A61M 2039/1077; A61M 25/0097; A61M 25/0606; A61M 25/0618; A61M 25/0631; A61M 39/10; A61M 5/3273
See application file for complete search history.

(56) References Cited

U.S. PATENT DOCUMENTS

| | | | |
|---|---|---|---|
| 4,952,207 A | 8/1990 | Lemieux | |
| 5,084,023 A | 1/1992 | Lemieux | |
| 5,304,144 A | 4/1994 | Brimhall | |

(Continued)

FOREIGN PATENT DOCUMENTS

| | | | |
|---|---|---|---|
| JP | 2003-180829 A | 7/2003 | |
| JP | 2011-519707 A | 7/2011 | |

(Continued)

OTHER PUBLICATIONS

Dual Protection Safety I.V. Catheter Supercath (TM) 5, a New Generation of Safety I.V. Catheter, www.medikit.co.jp/english/.

*Primary Examiner* — Brandy S Lee
(74) *Attorney, Agent, or Firm* — Dickinson Wright PLLC

(57) ABSTRACT

A catheter assembly comprising a catheter carried by a catheter adapter, a needle having a sharp distal tip and disposed in the catheter such that in a first needle position, the needle extends beyond the catheter, a damping mechanism fixed adjacent to a proximal end of the needle, and a barrel assembly configured to surround the damping mechanism, the barrel assembly including first and second inner diameters, wherein when the needle is retracted into the barrel assembly away from the first needle position, the needle moves in accordance with a needle retraction speed profile, and the needle retraction speed profile is based on the interaction between the first and second inner diameters of the barrel assembly and the damping mechanism.

14 Claims, 17 Drawing Sheets

(56) References Cited

U.S. PATENT DOCUMENTS

| | | | |
|---|---|---|---|
| 5,344,408 A | 9/1994 | Partika | |
| 5,419,766 A | 5/1995 | Chang et al. | |
| 5,501,675 A | 3/1996 | Erskine | |
| 5,575,777 A | 11/1996 | Cover et al. | |
| 5,817,069 A | 10/1998 | Arnett | |
| 5,967,490 A | 10/1999 | Pike | |
| 6,090,078 A * | 7/2000 | Erskine | A61M 25/0631 604/230 |
| 6,117,108 A * | 9/2000 | Woehr | A61M 25/0625 604/110 |
| 6,616,630 B1 | 9/2003 | Woehr et al. | |
| 7,214,208 B2 | 5/2007 | Vaillancourt | |
| 8,048,036 B2 | 11/2011 | Woehr | |
| 8,257,313 B2 | 9/2012 | McKinnon et al. | |
| 8,337,463 B2 | 12/2012 | Woehr et al. | |
| 8,529,515 B2 | 9/2013 | Woehr et al. | |
| 8,535,271 B2 | 9/2013 | Fuchs et al. | |
| 8,936,575 B2 | 1/2015 | Moulton | |
| 2002/0169418 A1 | 11/2002 | Menzi et al. | |
| 2003/0060774 A1 | 3/2003 | Woehr et al. | |
| 2006/0100577 A1 | 5/2006 | Shue et al. | |
| 2006/0155245 A1 | 7/2006 | Woehr | |
| 2006/0264828 A1 | 11/2006 | Woehr | |
| 2007/0255221 A1 | 11/2007 | Nakajima | |
| 2009/0281499 A1 | 11/2009 | Harding et al. | |
| 2011/0125097 A1 | 5/2011 | Shaw et al. | |
| 2012/0123354 A1 | 5/2012 | Woehr | |
| 2012/0271235 A1 | 10/2012 | Fuchs et al. | |
| 2012/0277680 A1 | 11/2012 | Woehr et al. | |
| 2017/0173304 A1 | 6/2017 | Teoh | |

FOREIGN PATENT DOCUMENTS

| | | |
|---|---|---|
| JP | 2012200425 A | 10/2012 |
| JP | 2013-022263 | 2/2013 |
| WO | 0018465 | 4/2000 |
| WO | 2016123620 | 8/2016 |

* cited by examiner

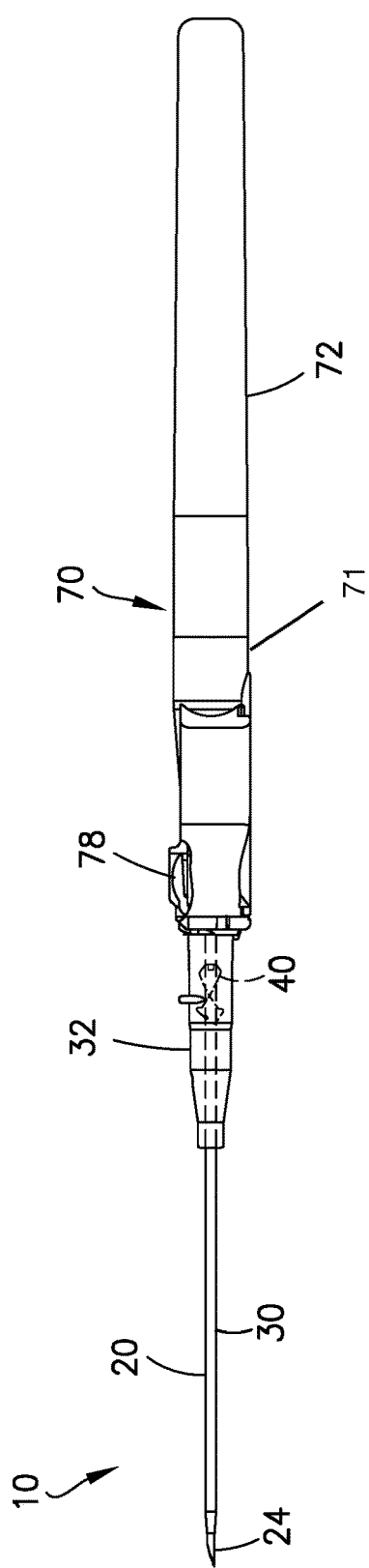
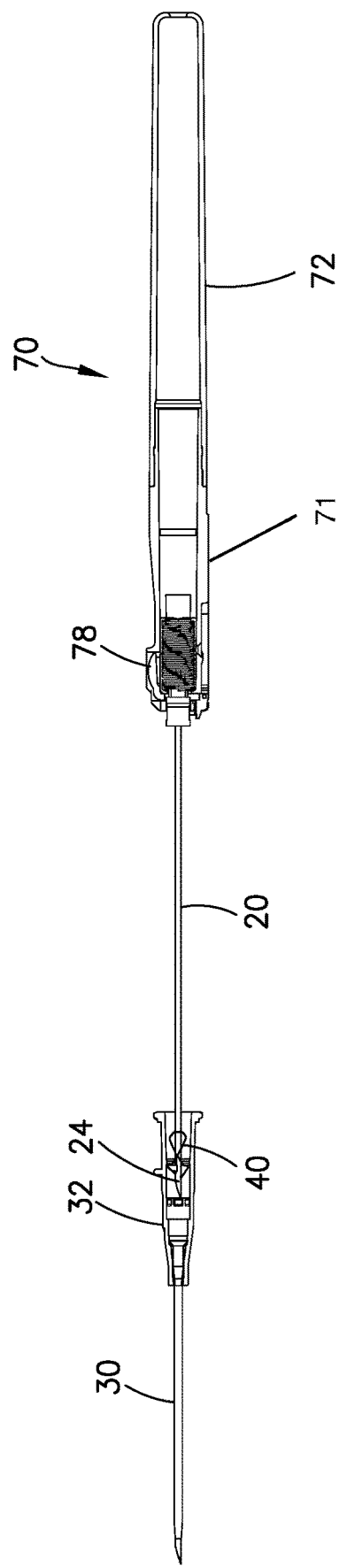
FIG.1
FIG.2

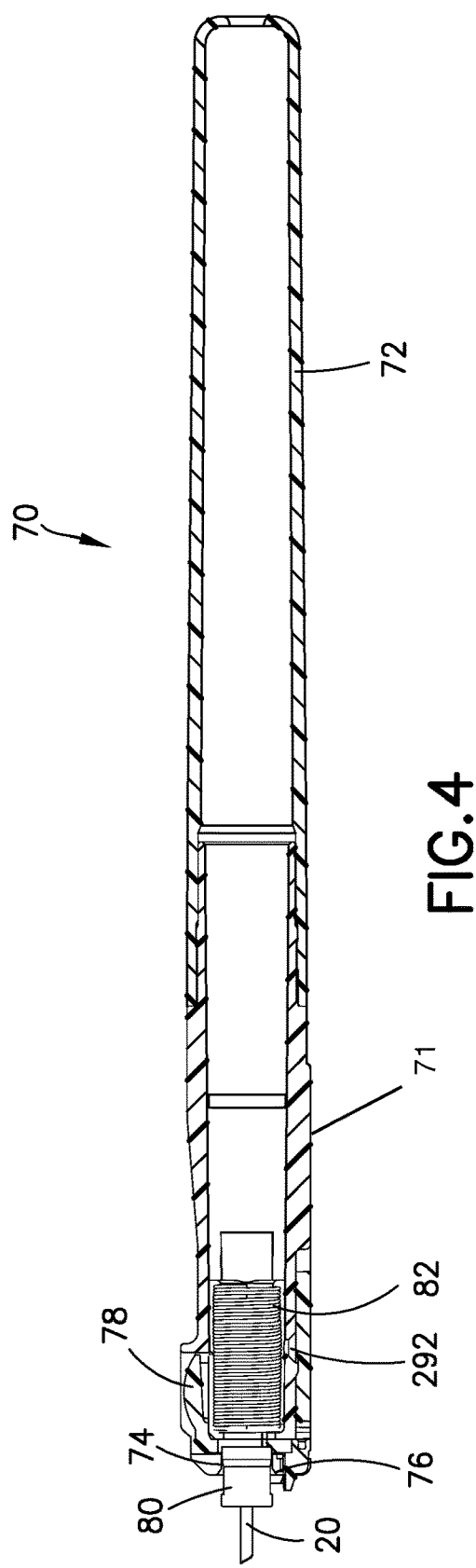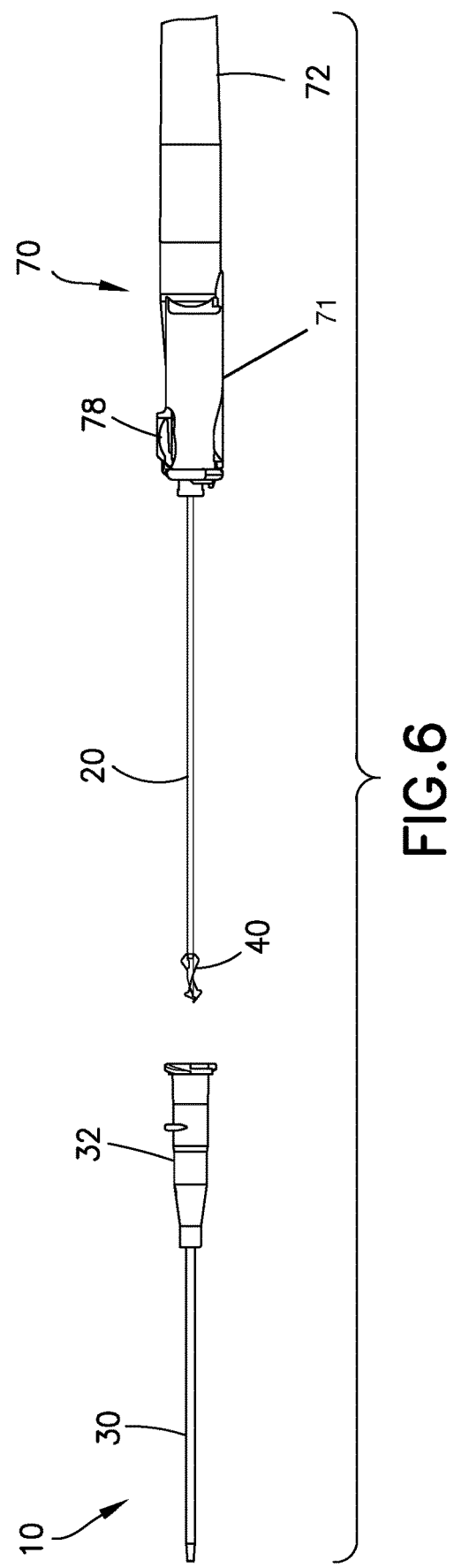

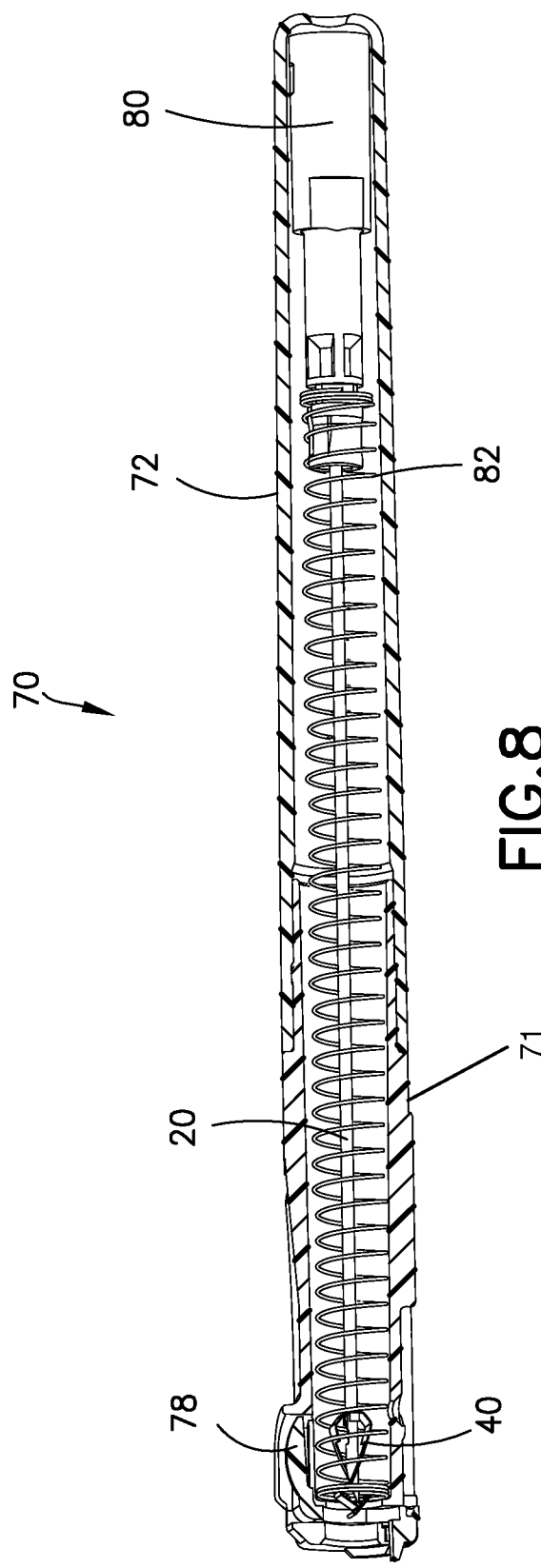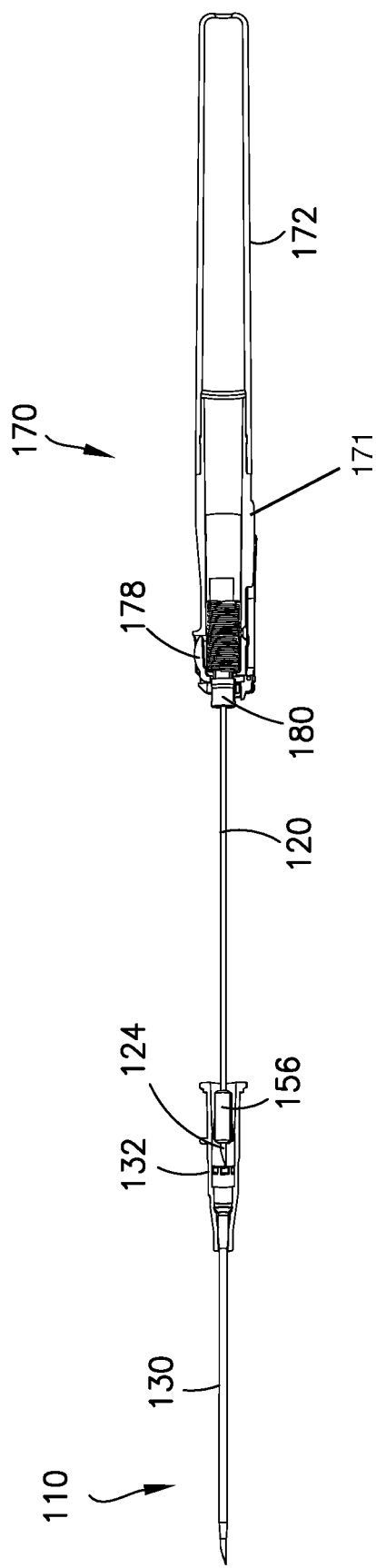

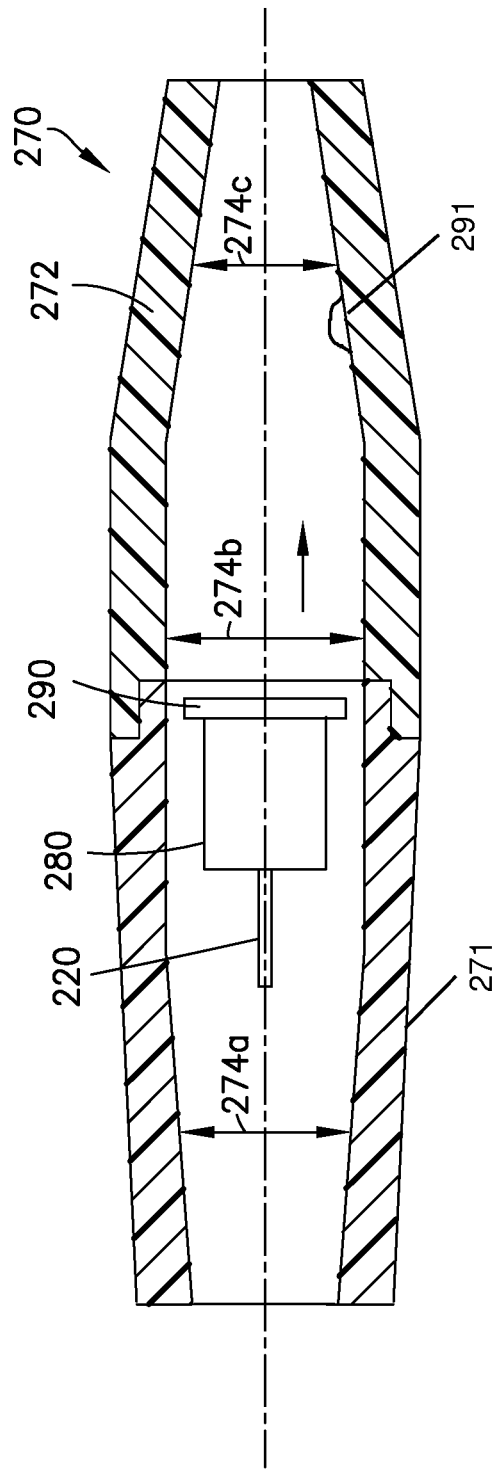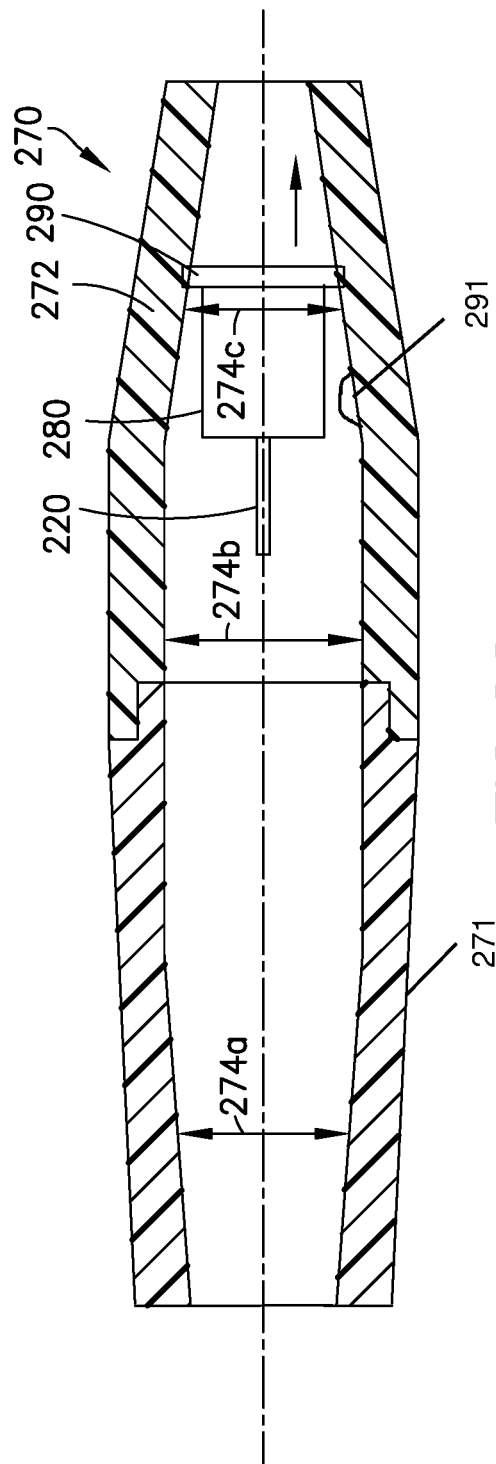

CATHETER ASSEMBLY

This application is a continuation of U.S. patent application Ser. No. 15/664,827 filed on Jul. 31, 2017, which is hereby incorporated by reference in its entirety.

FIELD

Various exemplary embodiments of the invention relate to needle protection and needle retraction in catheter assemblies.

BACKGROUND

Typical catheter assemblies incorporate one of two types of needle protection mechanisms. An active system is a needle protection mechanism that requires a separate user action to initiate needle protection, such as depression of an activation button to activate automatic and instantaneous needle retraction into a barrel assembly. This action would take place after the needle is withdrawn from a skin of a patient and from the catheter. On the other hand, a passive system is a needle protection mechanism that automatically protects the needle when a user manually retracts the needle from the catheter, typically using a spring clip and without requiring a separate user action. In other words, the needle is immediately protected when it is withdrawn from a skin of a patient and from the catheter.

Various disadvantages arise in each of the needle protection mechanisms. Specifically, in active systems, the user may neglect to depress the activation button or fail to perform the secondary user action to protect the needle. For example, when the activation button is not depressed, the used needle tip that is covered in blood is undesirably exposed from the body of a patient. In passive systems, the spring clip includes undesirable sharp edges, blood is exposed on the needle and the spring clip, and the spring clip can be manually manipulated to expose the distal tip of the needle after it is covered.

There are also various means of damping the speed of needle retraction into the barrel assembly of the catheter assembly. Some damping mechanisms include a silicone gel, an O-ring and a silicone washer. However, these damping mechanisms are not always able to adequately control the retraction speed of the needle.

SUMMARY OF THE INVENTION

It is an aspect of the present invention to provide a catheter assembly that incorporates both an active and passive system in a needle protection mechanism. Such a catheter assembly remedies the disadvantages above and improves needle protection and needle retraction. Specifically, the needle tip is enclosed by a spring clip and the needle is retracted into the barrel assembly. In this manner, if the user forgets to press the activation button, the distal tip is already protected by the spring clip. When the activation button is depressed, the needle and the spring clip retract into the barrel assembly, thereby protecting the user from all hazards. Accordingly, the catheter assembly advantageously prevents needle re-exposure and reduces blood exposure.

It is another aspect of the present invention to provide a controlled variable retraction speed of the needle into the barrel assembly of the catheter assembly. Such a catheter assembly advantageously provides slow needle retraction at the beginning and at the end of the needle travel to reduce blood splatter and provide smooth movement of the needle during retraction. A speed damping profile is advantageously used to control the speed of the needle retraction.

The foregoing and/or other aspects of the present invention can be achieved by providing a catheter assembly including a catheter carried by a catheter adapter, a needle having a sharp distal tip and disposed in the catheter such that in a first needle position, the needle extending beyond the catheter, a needle hub fixed adjacent to a proximal end of the needle, a clip disposed in the catheter adapter and cooperating with the needle, and a barrel assembly including an inner diameter, wherein when the needle is in a second needle position, the clip encloses the distal tip of the needle, and when the needle moves to a third needle position, the clip and the needle is disposed in the inner diameter of the barrel assembly.

The foregoing and/or other aspects of the present invention can also be achieved by a clip in a catheter assembly, the clip including one or more flexible arms that are configured to open and close the clip by biasing a needle in an open position and enclosing a distal tip of the needle in a closed position, an opening for the needle to pass through, one or more distal walls having a lip, the lip biasing the needle in the open position and the distal wall and the lip blocking the needle to close the clip in a closed position, and a rear wall connecting the one or more flexible arms, wherein the rear wall includes a tapered outer surface that is configured to guide movement of the clip into a barrel assembly.

The foregoing and/or other aspects of the present invention can additionally be achieved by a barrel assembly in a catheter assembly, the barrel assembly including a barrel and a handle each having an inner diameter, a needle hub fixed to a needle, a spring disposed between the needle hub and the barrel, and an activation button configured to engage and disengage the needle hub, wherein the inner diameter of the handle includes a tapered inner surface that is configured to guide movement of a clip into the handle and the barrel when the activation button is depressed.

The foregoing and/or other aspects of the present invention can further be achieved by providing a catheter assembly including a catheter carried by a catheter adapter, a needle having a sharp distal tip and disposed in the catheter such that in a first needle position, the needle extending beyond the catheter, a needle hub fixed adjacent to a proximal end of the needle and fixed to a damping mechanism, a clip being disposed in the catheter adapter, the clip cooperating with the needle, and a barrel assembly surrounding the needle hub, the barrel assembly including first, second and third inner diameters, wherein when the needle is in a second needle position, the clip encloses the distal tip of the needle, and when the needle moves to a third needle position, the needle is retracted into the barrel assembly via spring force from a spring, friction between the damping mechanism and the first inner diameter slows initial movement of the needle hub in the barrel assembly, clearance between the damping mechanism and the second inner diameter provides faster movement of the needle hub in the barrel assembly, and friction between the damping mechanism and the third inner diameter slows movement of the needle hub to a resting position at a proximal end of the barrel assembly.

The foregoing and/or other aspects of the present invention can also be achieved by providing a catheter assembly including a catheter carried by a catheter adapter, a needle having a sharp distal tip and disposed in the catheter such that in a first needle position, the needle extending beyond the catheter, a needle hub fixed adjacent to a proximal end of the needle and fixed to a first damping mechanism, a clip being disposed in the catheter adapter, the clip cooperating with the needle, a barrel assembly surrounding the needle hub, the barrel assembly including first and second inner diameters, a spring disposed between the barrel assembly and the needle hub, and a second damping mechanism disposed at a proximal end of the spring, wherein when the needle is in a second needle position, the clip encloses the distal tip of the needle, and when the needle moves to a third needle position, the needle is retracted into the barrel assembly via spring force from the spring, friction between the second damping mechanism and the spring slows initial movement of the needle hub in the barrel assembly, clearance between the first damping mechanism and the first inner diameter provides faster movement of the needle hub in the barrel assembly, and engagement of the first damping mechanism and the second inner diameter slows movement of the needle hub to a resting position at a proximal end of the barrel assembly.

The foregoing and/or other aspects of the present invention can additionally be achieved by providing a catheter assembly including a catheter carried by a catheter adapter, a needle having a sharp distal tip and disposed in the catheter, a needle hub fixed adjacent to a proximal end of the needle, a proximal end of the needle hub being fixed to a damping mechanism, a clip disposed in the catheter adapter, the clip cooperating with the needle, and a barrel assembly surrounding the needle hub, a proximal end of an inner surface of the barrel assembly including the damping mechanism, wherein when the needle is in a second needle position, the clip encloses the distal tip of the needle, and when the needle moves to a third needle position, the needle is retracted into the barrel assembly via spring force from a spring, and the damping mechanism and the spring slow initial movement of the needle hub in the barrel assembly, and when the needle hub approaches an end of travel, the damping mechanism and the spring slow movement of the needle hub to a resting position at a proximal end of the barrel assembly.

Finally, the foregoing and/or other aspects of the present invention can be achieved by providing a method for shielding and enclosing a needle of a catheter assembly, the method comprising removing a needle from a skin of a patient, the needle being fixed to a needle hub, pulling back the needle, via the needle hub, into a catheter and a catheter adapter from a first needle position to a second needle position, shielding, via a passive system, a distal tip of the needle using a clip, the needle being in the second needle position, and operating an active system, to move the needle, the clip and the needle hub from the second needle position to a third needle position where the needle, the clip and the needle hub are enclosed in a barrel assembly.

Additional and/or other aspects and advantages of the present invention will be set forth in the description that follows, or will be apparent from the description, or may be learned by practice of the invention.

BRIEF DESCRIPTION OF THE DRAWINGS

The above aspects and features of the present invention will be more apparent from the description for the exemplary embodiments of the present invention taken with reference to the accompanying drawings, in which:

FIG. 1 illustrates a side view of a first exemplary embodiment of a catheter assembly in a first needle position;

FIG. 2 illustrates a cross section view of the catheter assembly of FIG. 1 moving toward a second needle position;

FIG. 4 illustrates a partial cross section view of a barrel assembly of FIG. 2;

FIG. 6 illustrates a side view of the catheter assembly of FIG. 1 in a second needle position;

FIG. 8 illustrates a partial cross section view of the barrel assembly of FIG. 1 in the third needle position;

FIG. 10 illustrates a partial cross section view of a second exemplary embodiment of a catheter assembly moving toward a second needle position;

FIG. 21 illustrates a cross section view of the barrel assembly of FIG. 20 with the needle hub in an intermediate position; and FIG. 22 illustrates a cross section view of the barrel assembly of FIG. 20 with the needle hub in an end position;

DETAILED DESCRIPTION OF EXEMPLARY EMBODIMENTS

Figure 3:
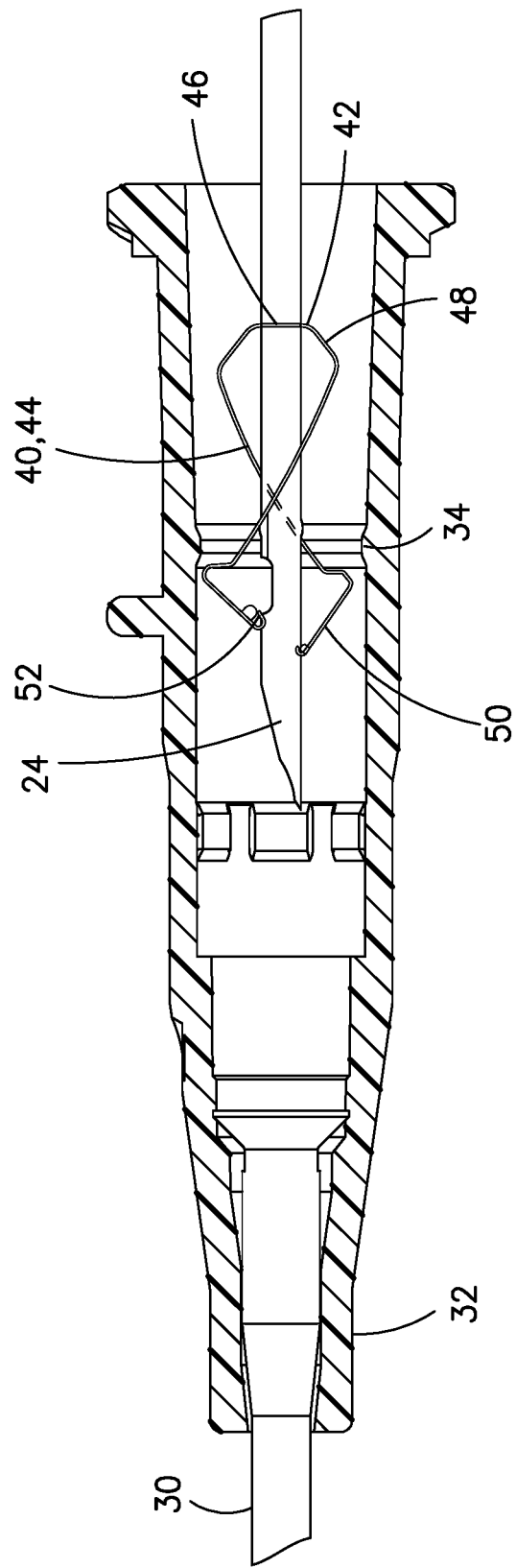
FIG. 3 illustrates a cross section view of a catheter adapter of FIG. 2.

FIGS. 1-9 illustrate a first exemplary embodiment of a catheter assembly 10. FIG. 1 illustrates the catheter assembly 10 in a first needle position ready for operation. According to one embodiment, the catheter assembly 10 includes a hollow introducer needle 20 having a sharp distal tip 24 for insertion in a skin of a patient. The needle 20 is disposed in a flexible catheter 30. The catheter 30 is used for medication delivery during use of the catheter assembly 10. In the first needle position, the sharp distal tip 24 of the needle 20 extends beyond the catheter 30 for insertion.

According to one embodiment, the catheter 30 and the needle 20 are carried or surrounded by a catheter adapter 32. FIG. 2 illustrates the needle 20 moving from the first needle position toward a second needle position after the user has placed the catheter 30 in the body of the patient and removed the needle 20 from the patient.

FIG. 3 illustrates, according to one embodiment, the catheter adapter 32 when the needle 20 is pulled back and approaching the second needle position. The catheter adapter 32 includes a retention feature 34 comprising a protrusion. The retention feature 34 retains a spring clip 40 when the spring clip 40 is in an open position as illustrated. Operation of the spring clip 40 is further described below.

The spring clip 40 is disposed in the catheter adapter 32 and cooperates with the needle 20 by selectively enclosing and locking the sharp distal tip 24 of the needle 20. Components and operation of the spring clip 40 are generally disclosed in U.S. Pat. No. 6,616,630, which is hereby incorporated by reference.

Specifically, according to one embodiment, the spring clip 40 includes an opening 42 where the needle 20 passes through. One or more flexible arms 44 of the spring clip 40, preferably two flexible arms 44, engage and bias the needle 20 in the open position prior to the needle entering the second needle position. The flexible arms 44 apply a spring force to two sides of the needle 20. In the first needle position and prior to the second needle position, the spring clip 40 is open to allow the needle 20 to pass through.

At the distal end of the flexible arms 44 include distal walls 50. The distal walls 50 are angled walls have lips 52 at one end which contact the needle 20. The lips 52 are folded inward portions of distal walls 50 of the spring clip 40.

The spring clip 40 further includes a rear wall 46. The rear wall 46 is substantially perpendicular to a longitudinal axis of the needle 20 and connects the two flexible arms 44 to each other. The rear wall 46 also includes the opening 42 as described above. The rear wall 46 preferably includes a tapered outer surface 48. In another embodiment, the tapered outer surface 48 comprises a radius or a chamfer. As further described below, the tapered outer surface 48 advantageously provides guided movement of the spring clip 40 into a handle 71 and a barrel 72.

Figure 5:
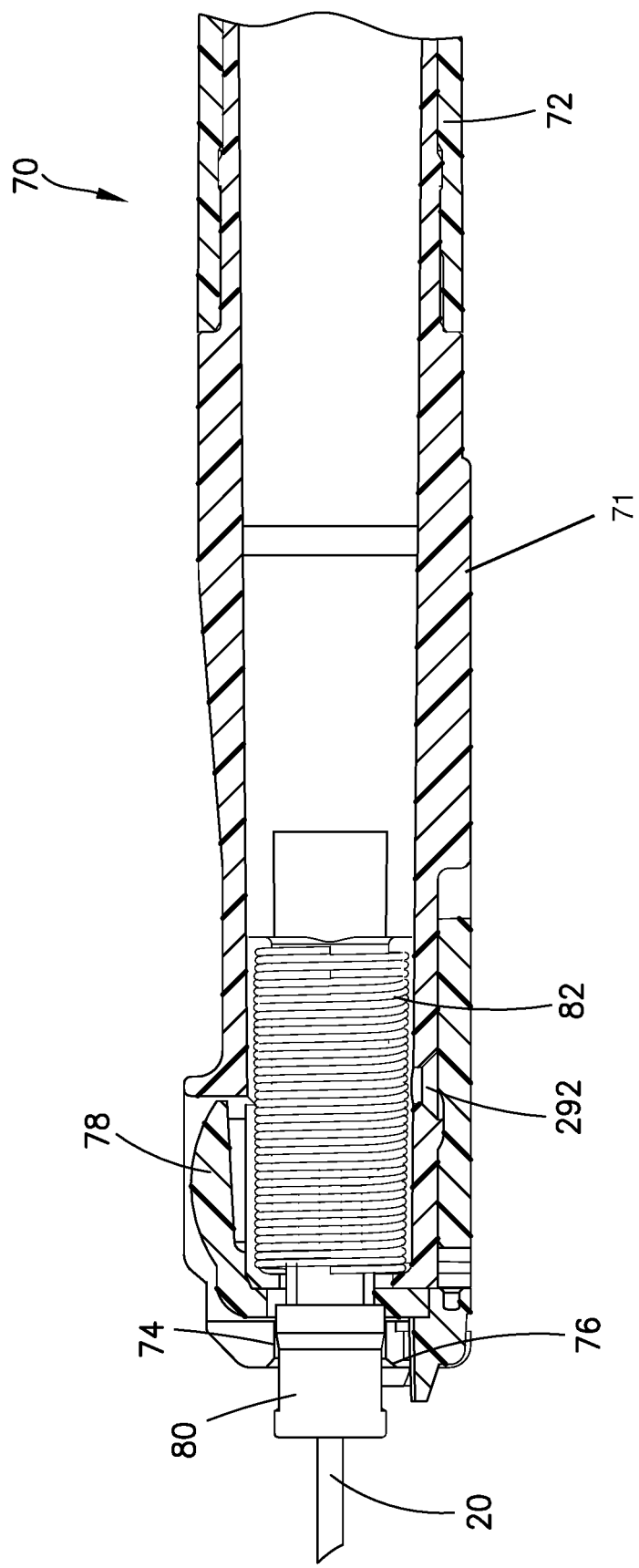
FIG. 5 illustrates a partial cross section view of a needle hub in the barrel assembly of FIG. 4.

FIGS. 4 and 5 illustrate the barrel assembly 70. According to one embodiment, the barrel assembly 70 includes the handle 71 (also referred to as a grip) and the barrel 72 (also referred to as a barrel housing). The handle 71 includes an inner diameter 74 and a tapered inner surface 76 at a distal end of the handle 71. In another embodiment, the tapered inner surface 76 comprises a radius or a chamfer. In another embodiment, the tapered inner surface 76 connects and provides a transition between an outer surface of the handle 71 and an inner surface of the handle 71. A distal end of the barrel 72 is connected to a proximal end of the handle 71 during operation.

In this embodiment, the catheter assembly 10 includes both the tapered inner surface 76 at the distal end of the handle 71 and the tapered outer surface 48 of the spring clip 40. In an alternate embodiment, the catheter assembly 10 includes only the tapered inner surface 76 at the distal end of the handle 71. Likewise, in an alternate embodiment, the catheter assembly 10 includes only the tapered outer surface 48 of the spring clip 40. In another embodiment, the catheter assembly 10 does not include either of the tapered inner surface 76 at the distal end of the handle 71 or the tapered outer surface 48 of the spring clip 40.

The tapered inner surface 76 is configured to cooperate with the tapered outer surface 48 of the spring clip 40 to advantageously engage and guide the spring clip 40 into the handle 71 and the barrel 72. Also, the tapered outer surface 48 advantageously engages the tapered inner surface 76 to center the spring clip 40 with respect to the handle 71 and the barrel 72. The handle 71 and the barrel 72 houses the components of the barrel assembly 70 as further described below.

The barrel assembly 70 further includes a needle hub 80. The needle hub 80 is fixed to the needle 20 and moves within the handle 71 and the barrel 72. Specifically, the needle hub 80 is fixed adjacent to a proximal end of the needle 20. As illustrated in FIG. 1, the needle hub 80 is connected to the catheter adapter 32 when the needle 20 is in the first needle position. Movement of the needle hub 80 causes the needle to retract from the second needle position to a third needle position as described below.

The handle 71 and the barrel 72 also interacts with an activation button 78 to engage and release the needle hub 80 and a spring 82. Specifically, the spring 82 is disposed about the needle 20 and extending between the needle hub 80 and the proximal end of the barrel 72. The activation button 78 contacts the needle hub 80 while the spring 82 is compressed. When the activation button 78 is depressed, the needle hub 80 no longer contacts the activation button 78 and the spring 82 is subsequently released to move the needle hub 80 through the handle 71 and toward a proximal end of the barrel 72. That is, the activation button 78 is movably mounted adjacent to the distal end of the barrel 72 and adapted for selective engagement with the needle hub 80 to hold the needle hub 80 adjacent to the distal end of the barrel 72 against the bias of the spring 82. In the first needle position, the needle 20 extends beyond the distal end of the handle 71 and the barrel 72 and through the catheter 30 with the catheter hub 32 adjacent to the distal end of the barrel 72. Operation of the activation button 78 is described in U.S. Pat. Nos. 5,501,675 and 5,797,880, which are hereby incorporated by reference. Further description of the operation is provided below.

According to one embodiment, FIG. 6 illustrates the catheter assembly 10 in the second needle position. In this position, the sharp distal tip 24 of the needle 20 is disposed in the spring clip 40 and shielded from an external environment. The user moving the needle 20 from the first needle position to the second needle position corresponds to a passive system. This is because the needle 20 is removed from the skin of the patient and the spring clip 40 protects the needle 20 in the same manual operation.

Figure 7:
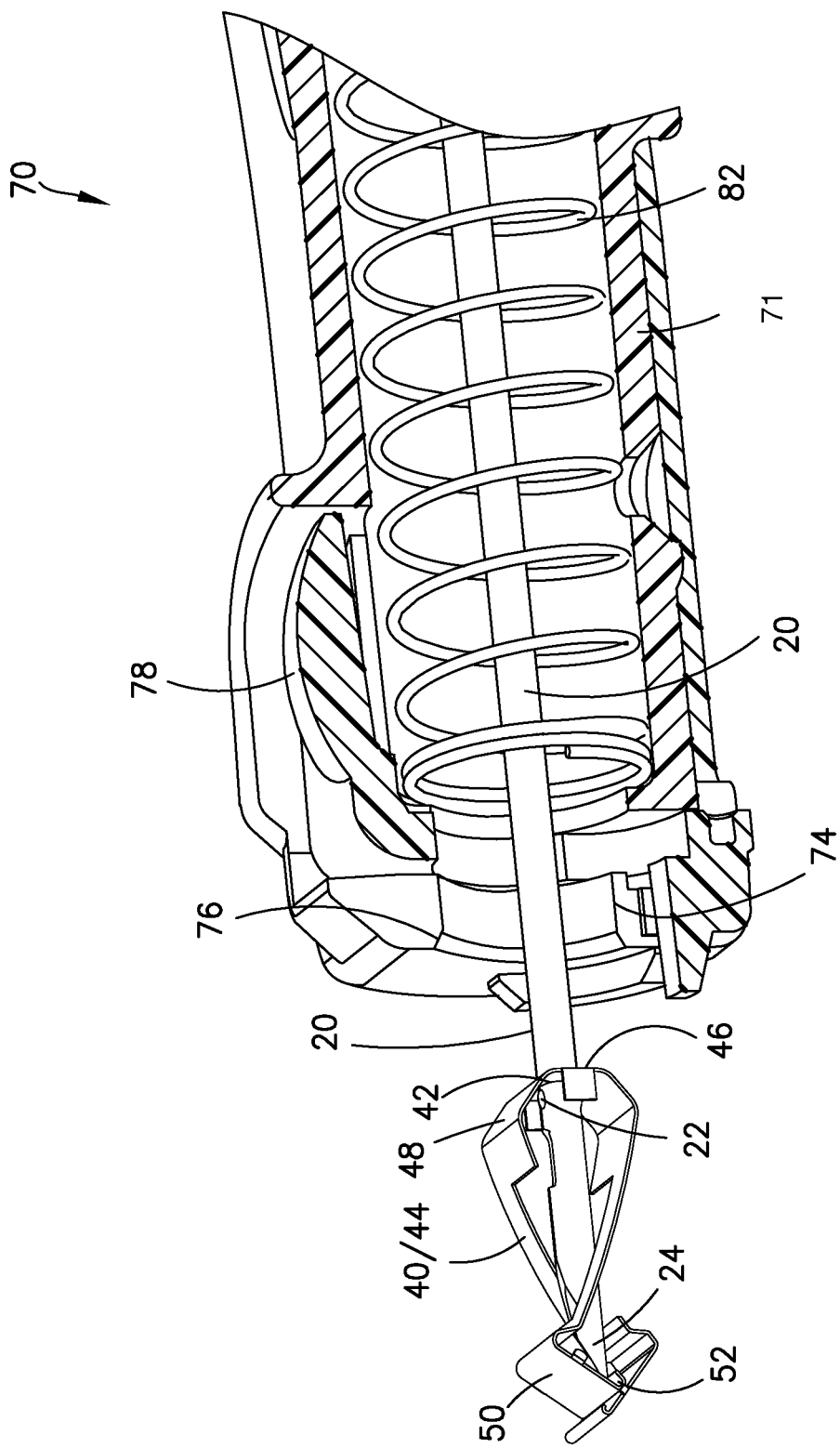
FIG. 7 illustrates a partial cross section view of the catheter assembly of FIG. 1 moving toward a third needle position.
Figure 9:
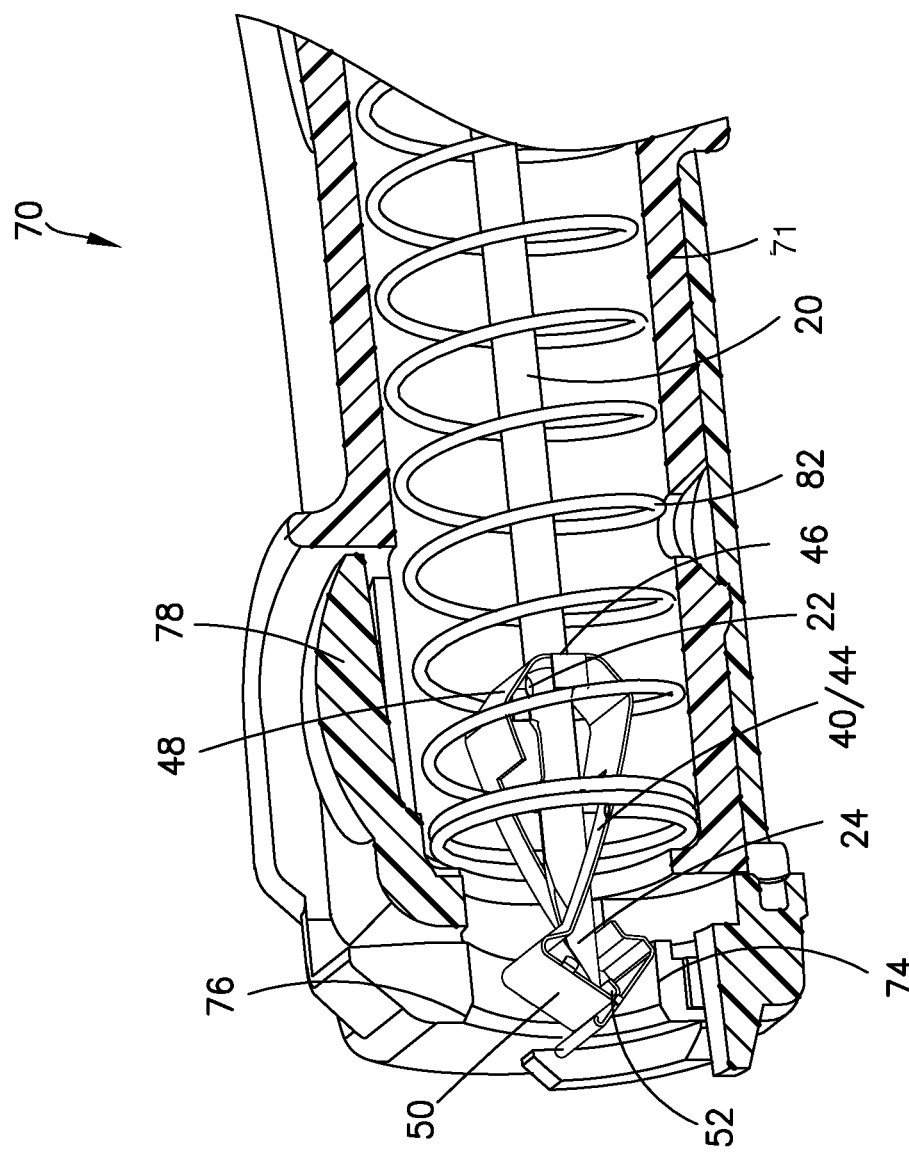
FIG. 9 illustrates a partial cross section view of a spring clip in the barrel assembly of FIG. 8.

As illustrated in FIG. 7, the spring clip 40 is in a closed position where the two flexible arms 44 bias against each other to enclose the sharp distal tip 24 of the needle 20. In another words, the distal walls 50 and the lips 52 overlap each other to close the spring clip 40 in a closed position. Specifically, the lip 52 of one flexible arm 44 contacts the distal wall 50 of the other flexible arm 44. The two flexible arms 44 of the spring clip 40 no longer bias the needle 20. Accordingly, the flexible arms 44 close the distal end of the spring clip 40 to prevent the needle 20 from exiting.

The needle 20 also includes a needle deformation 22 that provides the needle 20 with a local diameter that is larger than the diameter of the opening 42 in the spring clip 40. The needle deformation 22 prevents the needle 20 from exiting the spring clip 40 at its proximal end. Other means of retaining the sharp distal tip 24 inside the spring clip 40 includes the spring clip engaging a plate or a notch in the needle as described in U.S. Pat. No. 4,952,207, which is hereby incorporated by reference.

When the spring clip 40 is disposed in the closed position, the spring clip 40 no longer engages the retention feature 34 of the catheter adapter 32. Thus, as illustrated in FIG. 6, the spring clip 40 is no longer retained in the catheter adapter 32 and is now able to be removed from the catheter adapter 32.

FIG. 8 illustrates, according to one embodiment, the barrel assembly 70 when the catheter assembly 10 is in the third needle position. As described above, when the activation button 78 is depressed, the spring 82 and the needle hub 80 are released and retracted to the proximal end of the barrel 72. That is, the activation button 78 triggers operational movement of the needle 20, the spring clip 40 and the needle hub 80 to be enclosed in the barrel 72. During this movement, the tapered inner surface 76 of the inner diameter 74 of the handle 71 cooperates with the tapered outer surface 48 of the spring clip 40 to advantageously engage and guide the spring clip 40 into the handle 71 and the barrel 72. Also, the tapered outer surface 48 engages the tapered inner surface 76 to advantageously center the spring clip 40 with respect to the handle 71 and the barrel 72.

Movement from the second needle position to the third needle position corresponds to an active system. This is because a secondary step subsequent to the initial withdrawal of the needle 20 from the skin of the patient takes place. Specifically, in this secondary step, the user depresses the activation button 78 causing the needle 20 to automatically retract via a spring force from the spring 82. Thus, in this third needle position, the sharp distal tip 24 and the spring clip 40 are safely enclosed in the barrel 72.

According to one embodiment, if the catheter 30 is inserted into the skin of a patient and the activation button 78 is depressed, the needle 20 and the needle hub 80 are immediately withdrawn into the barrel assembly 70. Under this scenario, the tip shielding of the second needle position automatically takes place. This movement corresponds to the passive system.

Typically, in the prior art, spring clips are not retracted into a barrel. Either spring clips are used to cover a sharp distal tip of a needle or a needle without a spring clip is retracted into the barrel. The catheter assembly 10 disclosed herein advantageously combines an active and a passive system to ensure increased safety to the user and reduces blood exposure and splatter. The catheter assembly 10 improves operation by providing the tapered inner surface 76 of the inner diameter 74 of the handle 71 to cooperate with the tapered outer surface 48 of the spring clip 40.

FIGS. 10-19 illustrate a second exemplary embodiment of a catheter assembly 110. The catheter assembly 110 is a modified version of the catheter assembly 10 described above with the following differences. FIG. 10 illustrates the catheter assembly 110 when the user removes a needle 120 from a distal end of a catheter 130 and positions a sharp distal tip 124 of the needle 120 into a catheter adapter 132.

Figure 11:
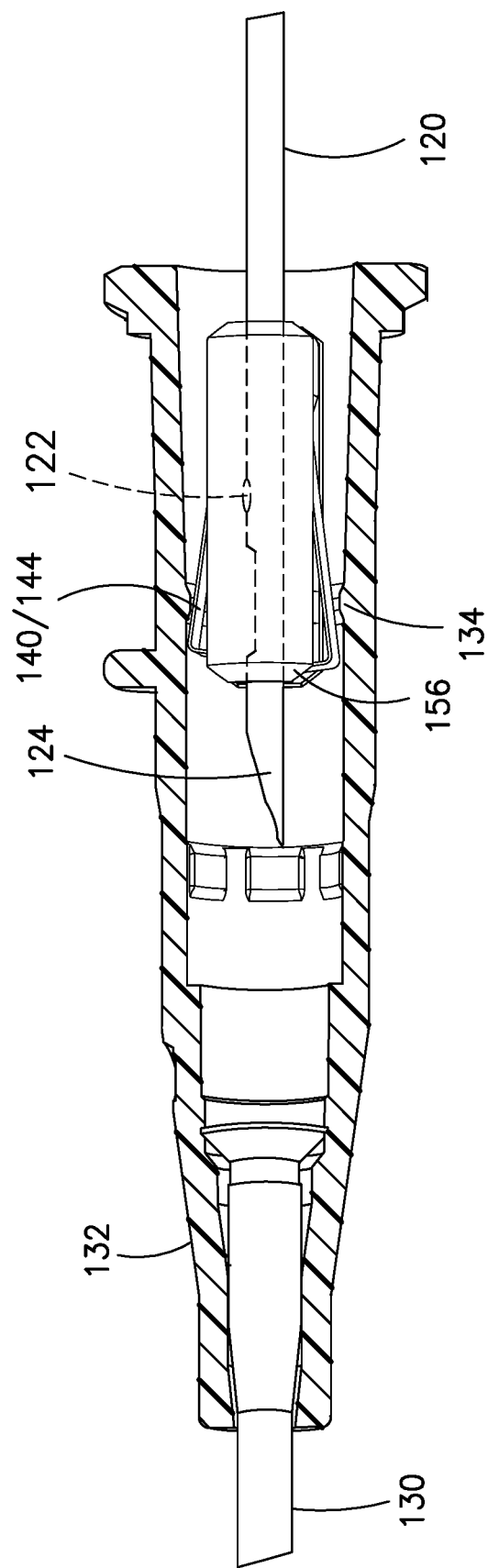
FIG. 11 illustrates a partial cross section view of a catheter adapter of FIG. 10.

FIG. 11 illustrates, according to one embodiment, the needle 120 inside the catheter adapter 132. As similarly described in the previous embodiment, a spring clip 140 selectively opens and closes to expose and enclose the sharp distal tip 124 of the needle 120. The spring clip 140 includes an opening 142 for the needle 120 to travel through. The spring clip 140 also includes a curved portion 154, distal walls 150 and lips 152 to enclose the sharp distal tip 124. The curved portion 154 is configured so that flexible arms 144 appropriately flex between open and closed positions of the spring clip 140. Additionally, the spring clip 140 includes a rear wall 146 and a tapered outer surface 148 at a proximal end of the spring clip 140. The catheter adapter 132 further includes a retention feature 134 that retains the spring clip 140 via the flexible arms 144 until the spring clip 140 is closed.

Figure 12:
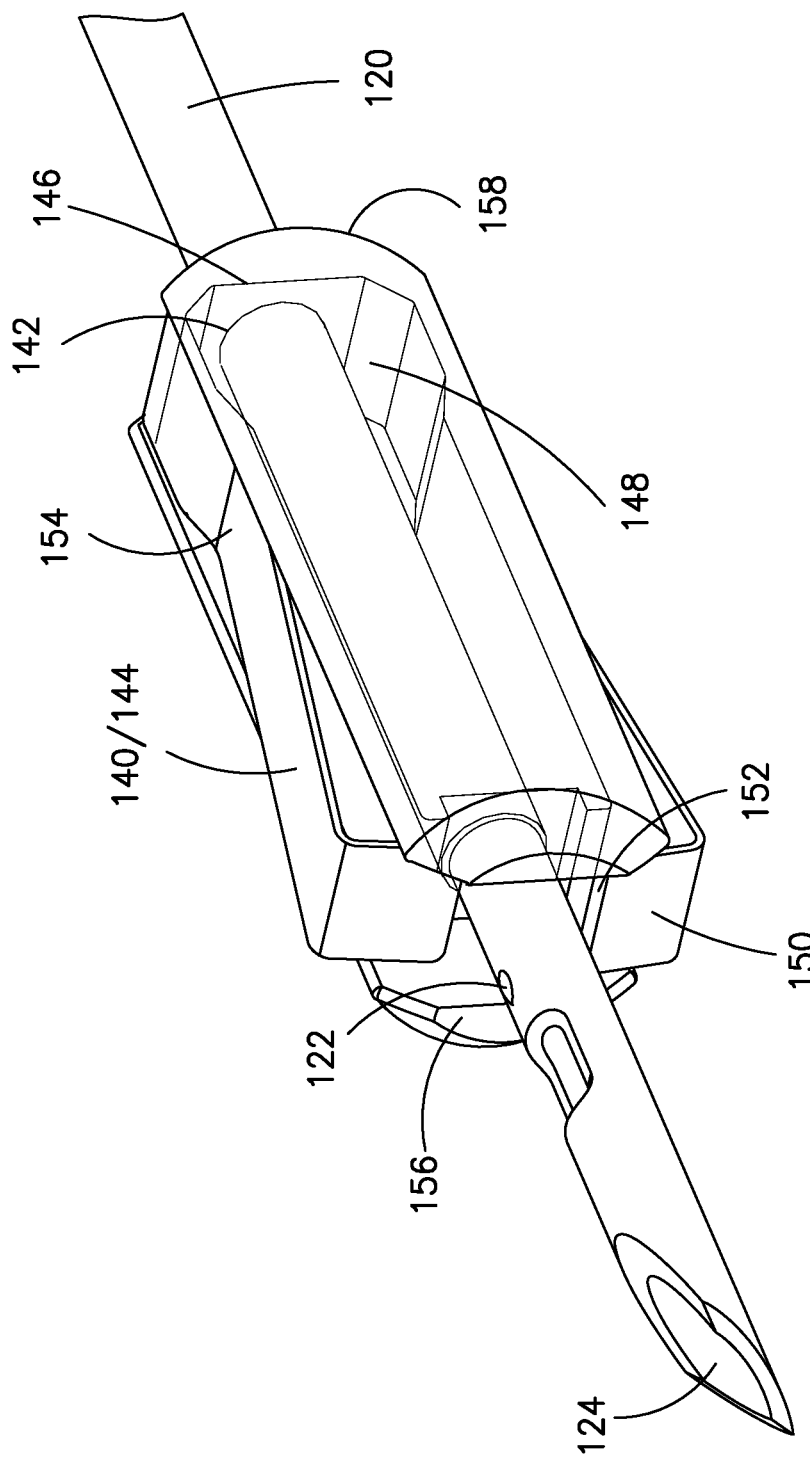
FIG. 12 illustrates a transparent perspective view of a spring clip and a clip housing of FIG. 11 moving toward a second needle position.

According to one embodiment, FIGS. 11 and 12 also illustrate a clip housing 156 that partially surrounds the spring clip 140. Features and operation of the clip housing 156 are similarly disclosed in U.S. patent application Ser. No. 15/481,166 filed on Apr. 6, 2017, which is hereby incorporated by reference. Specifically, the clip housing 156 advantageously covers any sharp edges in the spring clip 140 to protect the user from inadvertent contact. The clip housing 156 also includes locking and/or engagement features to prevent inadvertent separation from the spring clip 140.

The flexible arms 144 of the spring clip 140 extend outside of the clip housing 156 in the open position of the spring clip 140. The clip housing 156 of this embodiment also advantageously includes a tapered outer surface 158 at a distal end of the clip housing 156. In another embodiment, the tapered outer surface 158 comprises a radius or a chamfer. The tapered outer surface 158 is configured to advantageously provide guided movement of the clip housing 156 into a handle 171 and a barrel 172 as further described below and as similarly described in the previous embodiment. Also, the tapered outer surface 158 advantageously centers the spring clip 140 with respect to the handle 171 and the barrel 172. Accordingly, the tapered outer surface 158 of the clip housing 156 cooperates with the tapered outer surface 148 at the rear wall 146 of the spring clip 140 to advantageously provide smooth travel into the handle 171 and the barrel 172.

Figure 13:
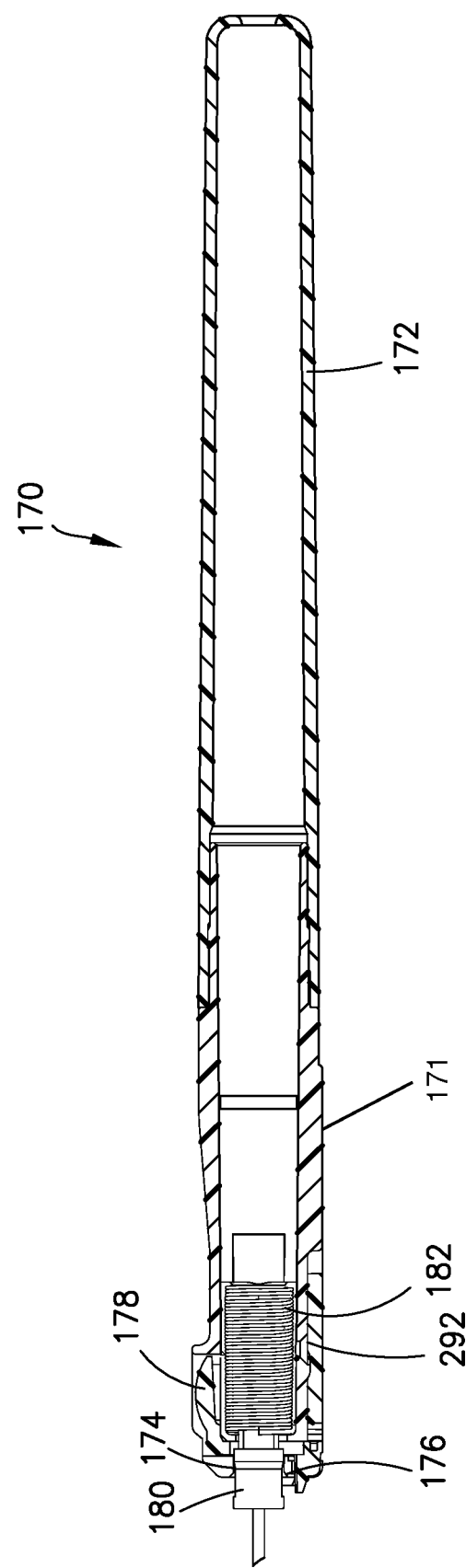
FIG. 13 illustrates a partial cross section view of a barrel assembly of FIG. 10.
Figure 14:
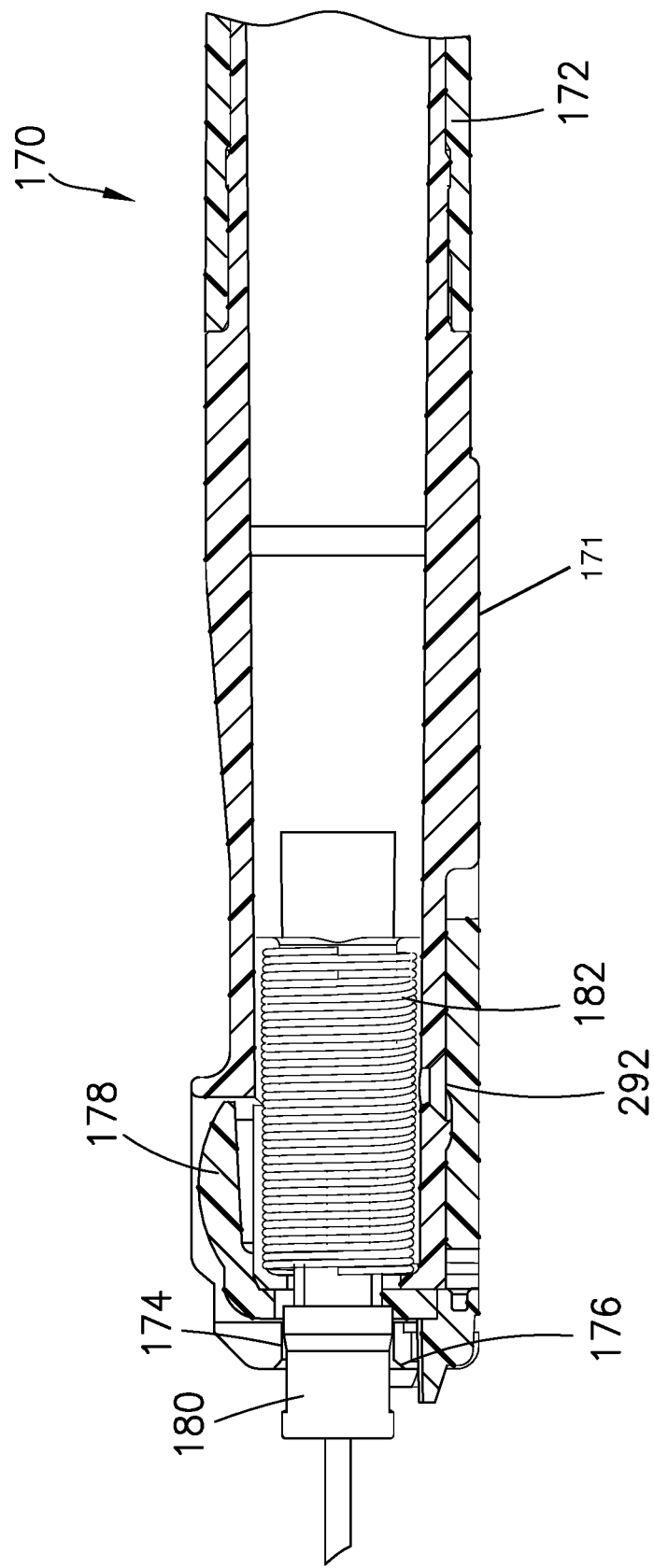
FIG. 14 illustrates a partial cross section view of a needle hub in the barrel assembly of FIG. 13.

According to one embodiment, FIGS. 13 and 14 illustrate a barrel assembly 170. As similarly described in the previous embodiment, the barrel assembly 170 includes the handle 171 having an inner diameter 174. The inner diameter 174 includes a tapered inner surface 176 disposed at a distal end of the handle 171. The tapered inner surface 176 of the inner diameter 174 of the handle 171 cooperates with the tapered outer surface 148 of the spring clip 140 and the tapered outer surface 158 of the clip housing 156 to advantageously engage and guide the spring clip 140 and the clip housing 156 into the handle 171 and the barrel 172. Also, the tapered outer surface 148 of the spring clip 140 and the tapered outer surface 158 of the clip housing 156 engage the tapered inner surface 176 to advantageously center the spring clip 140 and the clip housing 156 with respect to the handle 171 and the barrel 172.

As similarly described in the previous embodiment, the barrel assembly 170 further includes an activation button 178 and a spring 182 that cooperates with a needle hub 180 for retraction. The needle 120 is fixed to the needle hub 180 so that the needle 120 is retracted into the barrel 172 when the activation button 178 is depressed.

Figure 15:
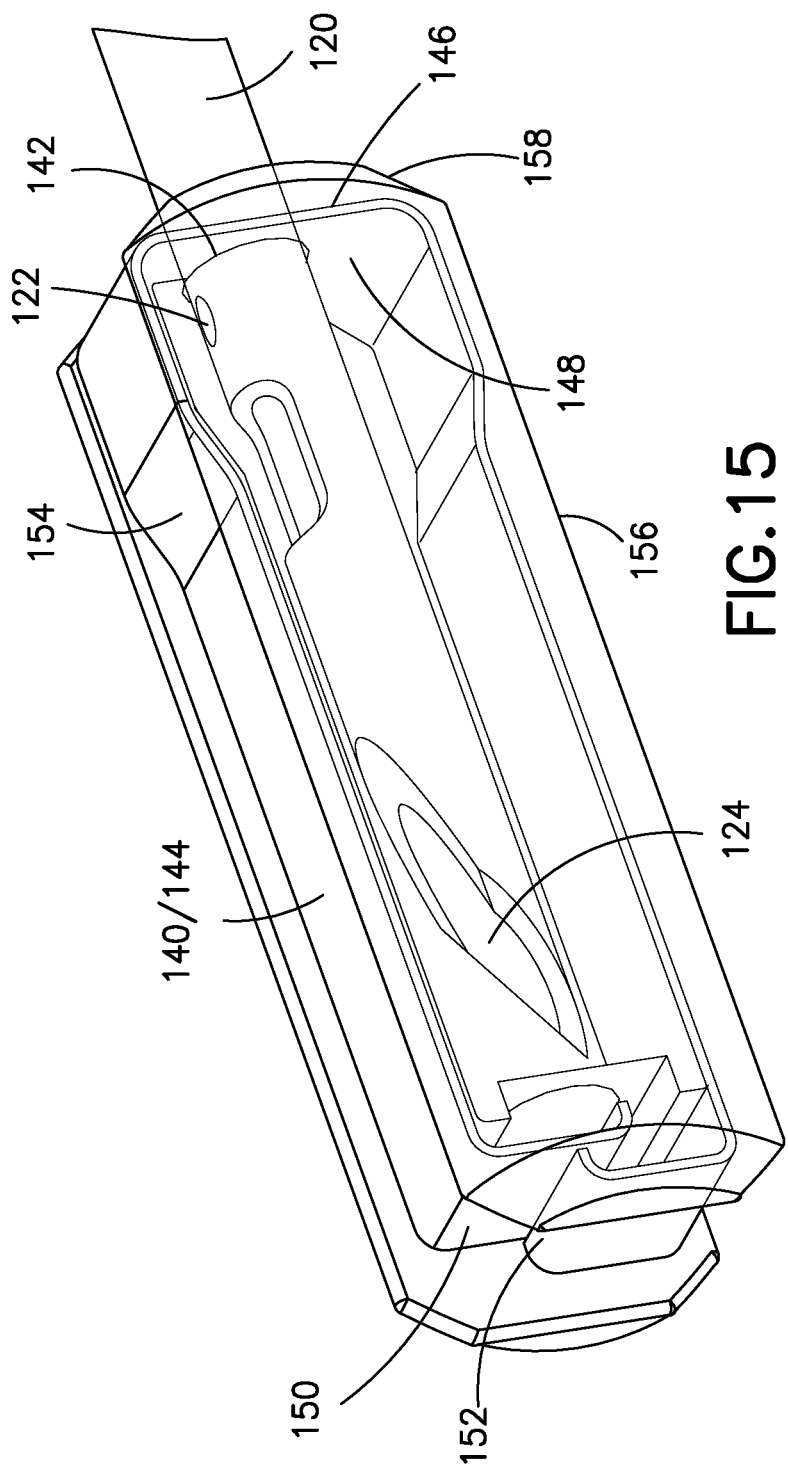
FIG. 15 illustrates a transparent perspective view of the spring clip and the clip housing of FIG. 10 in the second needle position.

FIG. 15 illustrates, according to one embodiment, the spring clip 140 being substantially disposed in the clip housing 156 and in a closed position where the needle is in a second needle position. Specifically, the distal walls 150 are offset and the lip 152 of one of the distal walls 150 contacts the other distal wall 150 to block the distal tip 124 of the needle 120 from exiting the clip housing 156. Also, after the spring clip 140 is in the closed position, a distal portion of the spring clip 140 may extend beyond the clip housing 156.

Figure 16:
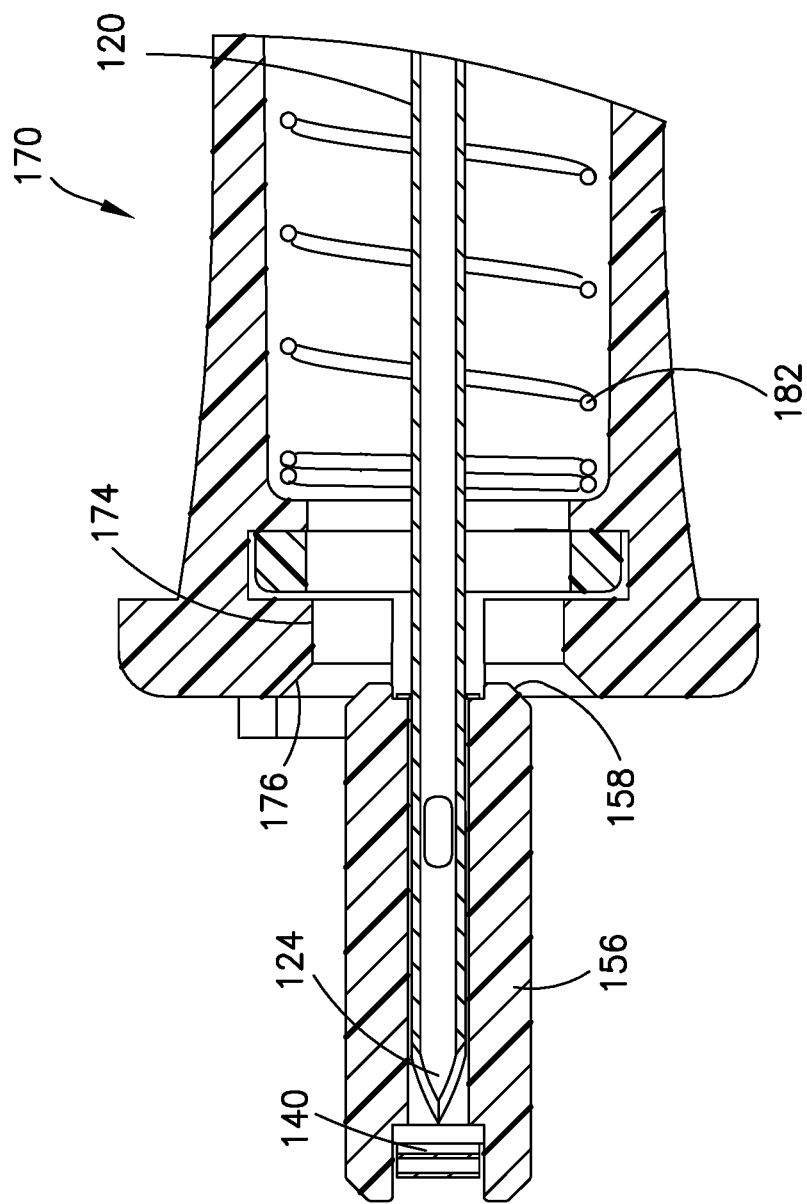
FIG. 16 illustrates a top section view of the spring clip, clip housing and barrel assembly of FIG. 10 in the second needle position.
Figure 17:
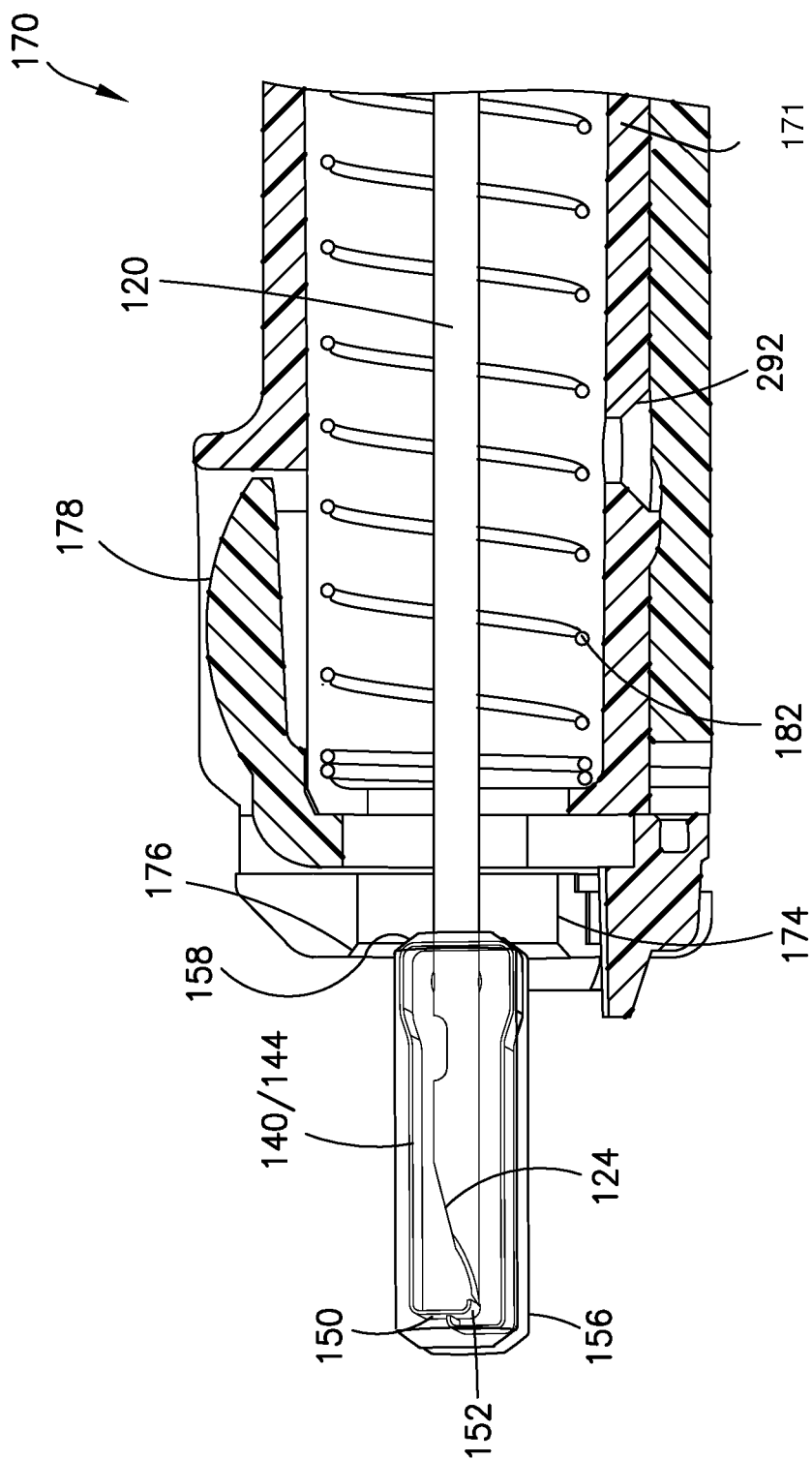
FIG. 17 illustrates a transparent cross section view of the spring clip, clip housing and the barrel assembly of FIG. 10 in the second needle position.

According to one embodiment, FIG. 16 illustrates a top section view and FIG. 17 illustrates a cross section view of the spring clip 140 and the clip housing 156. Both of these figures illustrate the spring clip 140 and the clip housing 156 being retracted into the barrel 172 from the second needle position to a third needle position.

Figure 18:
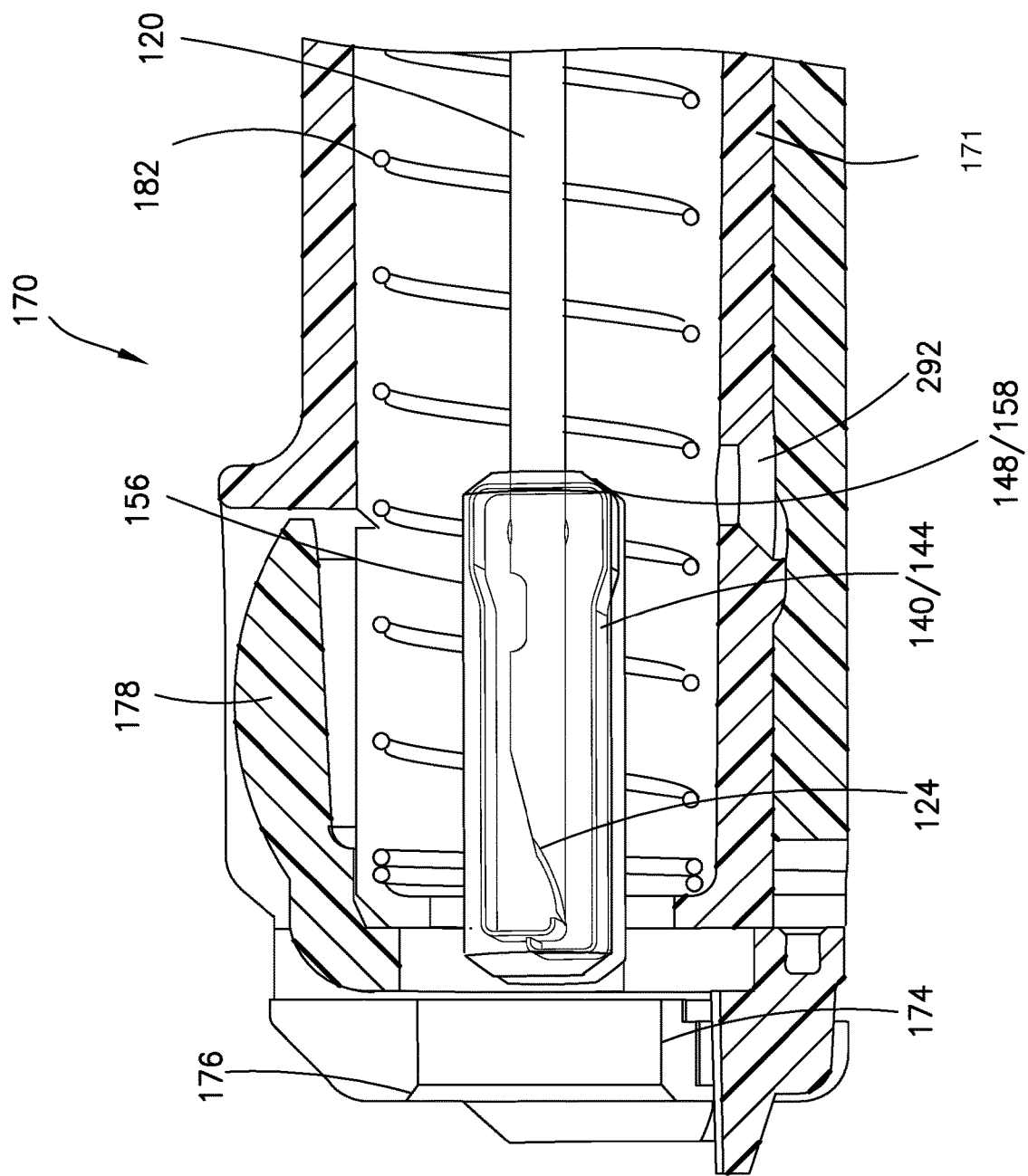
FIG. 18 illustrates a transparent cross section view of the spring clip, clip housing and the barrel assembly of FIG. 10 in a third needle position.
Figure 19:
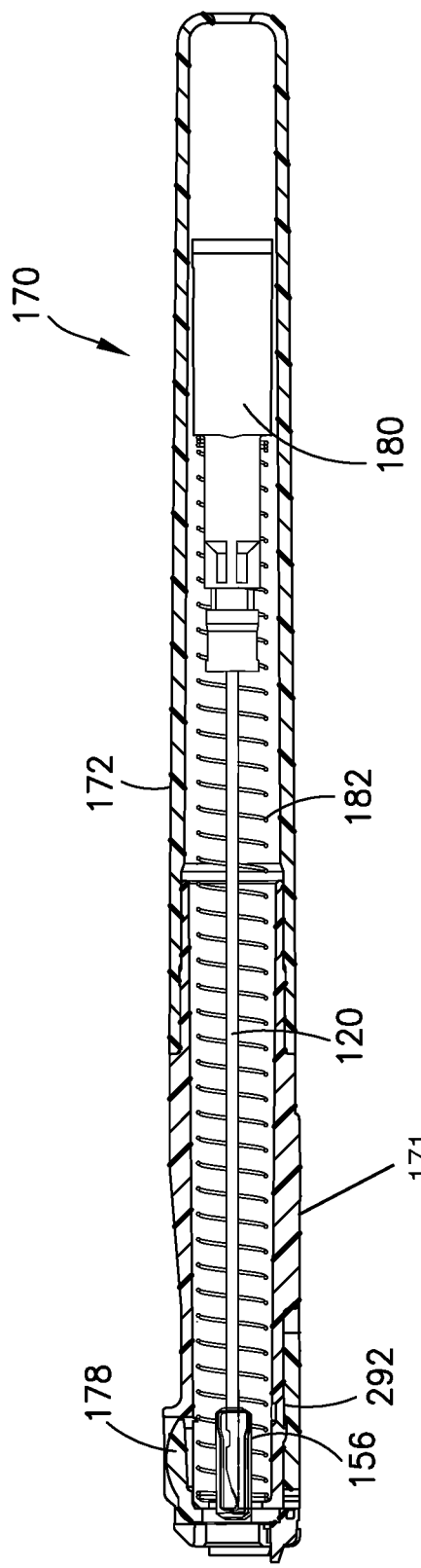
FIG. 19 illustrates a partial cross section view of the barrel assembly of FIG. 10 in the third needle position.

As similarly described in the previous embodiment, FIGS. 18 and 19 illustrate the spring clip 140 and the clip housing 156 in the barrel 172. This is the third needle position of the needle 120 of the catheter assembly 110.

Figure 20:
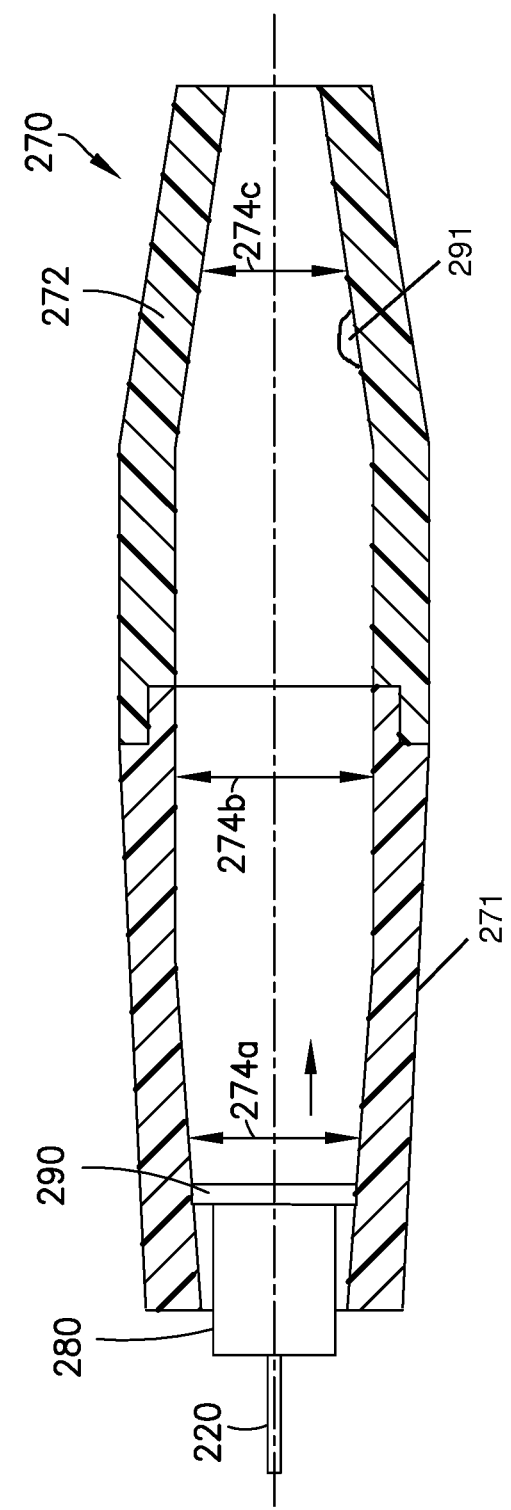
FIG. 20 illustrates a cross section view of a third exemplary embodiment of a barrel assembly with a needle hub in a starting position.

FIGS. 20-22 illustrate a third exemplary embodiment of a barrel assembly 270. The barrel assembly 270 is a modified version of the barrel assembly 70, 170 described above with the following improvements to control a retraction speed of a needle 220 in a handle 271 and a barrel 272.

In the previous embodiments described above, when the activation button 78, 178 is depressed, the needle hub 80, 180 is retracted into the handle 71, 171 and the barrel 72, 172 via force from the spring 82, 182. However, the retraction speed of the needle hub 80, 180 may be high, which can cause blood to splatter during retraction. Various damping mechanisms have been used in the prior art including a silicone gel, bladder air vents, O-rings, a crushable filter and spring compression nodes as described in U.S. Pat. Nos. 5,575,777, 5,702,367 and 6,090,078, which are hereby incorporated by reference.

According to one embodiment, the barrel assembly 270 provides a controlled variable retraction speed of the needle 220 into the handle 271 and the barrel 272 of the catheter assembly. Specifically, the handle 271 includes a first inner diameter 274a, a second inner diameter 274b and a third inner diameter 274c. The first inner diameter 274a and the third inner diameter 274c are substantially similar. Also, the second inner diameter 274b is greater than each of the first inner diameter 274a and the third inner diameter 274c, respectively. The three inner diameters 274a, 274b, 274c are connected via inner diameter tapers to provide a continuous changing inner diameter.

The barrel assembly 270 further includes a needle hub 280 that secures the needle 220. A first damping mechanism 290 is advantageously fixed to a proximal end of the needle hub 280. In one embodiment, the first damping mechanism 290 is a silicone washer or a silicone disc.

In operation of the catheter assembly, when the activation button 78, 178 is depressed, an outer diameter of the first damping mechanism 290 is in frictional contact with the first inner diameter 274a. This is because the first inner diameter 274a is smaller than the outer diameter of the first damping mechanism 290. As a result, the needle hub 280 and needle 220 advantageously begin to move slowly into the handle 271 and the barrel 272.

As the needle hub 280 continues to move in the handle 271 and the barrel 272, the inner diameter increases in size to the second inner diameter 274b. The second inner diameter 274b is larger than the outer diameter of the first damping mechanism 290. Accordingly, there is clearance (significantly reduced frictional contact) between the second inner diameter 274b and the first damping mechanism 290. As a result, the needle hub 280 advantageously picks up speed and moves faster through the handle 271 and the barrel 272.

As the needle hub 280 approaches the end of its travel in the barrel 272, the inner diameter of the barrel 272 decreases in size to the third inner diameter 274c. The outer diameter of the first damping mechanism 290 is in frictional contact with the third inner diameter 274c. This is because the third inner diameter 274c is smaller than the outer diameter of the first damping mechanism 290. As a result, the needle hub 280 advantageously slows down in speed as it approaches the end of travel in the barrel 272.

The catheter assembly incorporating the barrel assembly 270 of this embodiment advantageously provides slow needle retraction at the beginning and at the end of the needle travel to reduce blood splatter and provide smooth movement of the needle 220 and needle hub 280 during retraction. The changing diameters in the handle 271 and the barrel 272 advantageously provide a speed damping profile to control the speed of the needle retraction at various positions.

The speed damping profile can be adjusted based on the desired retraction speed of the needle 220 and the needle hub 280. According to one embodiment, the third inner diameter 274c is smaller than the first inner diameter 274a to advantageously provide a slower retraction speed at the end of travel compared to at the beginning of travel. According to another embodiment, the first inner diameter 274a is smaller than the third inner diameter 274c to advantageously provide a slower retraction speed at the beginning of travel compared to at the end of travel. According to one embodiment, the second inner diameter 274b is substantially similar to the first and third inner diameters 274a, 274c to advantageously provide a slow retraction speed of the needle 220 and needle hub 280 throughout travel in the handle 271 and the barrel 272.

According to one embodiment, the width of each of the inner diameters 274a, 274b, 274c are varied to adjust the speed damping profile. Specifically, the width of the inner diameters 274a, 274b, 274c advantageously control an amount of time for retraction at each portion of the handle 271 and the barrel 272 as the needle 220 and the needle hub 280 travel through the handle 271 and the barrel 272. The amount of friction between the inner diameters 274a, 274b, 274c and the first damping mechanism 290 (how much interference is present), as well as the strength of the spring 82, 182 also advantageously controls the amount of time for retraction at each portion of the handle 271 and the barrel 272.

A fourth exemplary embodiment of a catheter assembly is a modified version of the barrel assembly 270 described above with the following differences. Specifically, the handle 271 and the barrel 272 include a first and second inner diameter 274a, 274b as similarly described above. The barrel assembly 270 also includes a first damping mechanism 290 being fixed at a proximal end of a needle hub 280. The barrel assembly 270 further includes a second damping mechanism 291. The first damping mechanism 290 is a silicone washer as similarly described above and the second damping mechanism 291 is a silicone gel. The silicone gel 291 is applied at a proximal end of the spring 82, 182 prior to retraction. FIGS. 4, 5, 13, 14, 17-19 illustrate an exemplary access hole 292 that is provided in the handle 71, 171 for the user to supply the silicone gel 291.

In operation of the catheter assembly with the barrel assembly 270 of this embodiment, when the activation button 78, 178 is depressed, an outer diameter of the first damping mechanism 290 is in frictional contact with the first inner diameter 274a. This is because the first inner diameter 274a is smaller than the outer diameter of the first damping mechanism 290. As a result, the needle hub 280 and needle 220 advantageously begin to move slowly into the handle 271 and the barrel 272 during retraction.

As the needle hub 280 continues to move in the handle 271 and the barrel 272, the inner diameter of the handle 271 and the barrel 272 increases to the second inner diameter 274b. The second inner diameter 274b is larger than the outer diameter of the first damping mechanism 290. Accordingly, there is significantly less frictional contact between the second inner diameter 274b and the first damping mechanism 290. As a result, the needle hub 280 advantageously picks up speed and moves faster through the handle 271 and the barrel 272 during retraction.

As the needle hub 280 approaches the end of its travel in the barrel 272, the spring 82, 182 advantageously begins to move through the applied silicone gel of the second damping mechanism 291. The silicone gel of the second damping mechanism 291 resists the extension of the spring 82, 182 to advantageously slow the retraction of the needle 220 and the needle hub 280. Accordingly, the combination of the first and second damping mechanisms 290, 291 advantageously provides a similar speed damping profile during needle retraction as the third embodiment described above.

This configuration advantageously reduces the manufacturing complexities of more than two controlled inner diameters in the handle 271 and the barrel 272. Also, the combination of the silicone washer 290 and the silicone gel 291 advantageously provide similar damping characteristics while reducing blood splatter and provides smooth movement of the needle 220 and the needle hub 280 during retraction.

According to one embodiment, the silicone gel of the second damping mechanism 291 is applied to the distal end of the spring 82, 182, as well as the proximal end of the inner diameter of the handle 271. In this manner, the silicone gel 291 is in contact with the spring 82, 182 in the compressed state, as well as when the spring 82, 182 moves to its extended state. Accordingly, the silicone gel 291 resists the extension of springs 82, 182 while contacting the needle hub 280 to slow its movement throughout travel. Applying silicone gel 291 in this manner advantageously allows coils of the springs 82, 182 to expand one at a time, instead of all at once.

Such a configuration advantageously improves the accuracy of the speed damping profile during needle retraction, particularly at the beginning of travel by slowly permitting the initial movement of the needle hub 280 after initial activation. This configuration also advantageously avoids the use of a silicone washer 290, which is susceptible to providing excessive friction upon activation. Under this scenario, the frictional force is greater than the spring force and thus, the needle 220 does not retract and remains in an unsafe condition. Accordingly, the silicone gel 291 advantageously provides a strong solution for the initial, activation phase.

According to one embodiment, the silicone gel 291 is provided to the distal end of the spring 82, 182 in the compressed state and the silicone washer 290 is fixed to the proximal end of the needle hub 280. The silicone washer 290 only significantly contacts the inner diameter of the barrel 272 near the end of travel to provide a significant frictional force. In this manner, the silicone gel 291 advantageously provides a strong solution for the initial, activation phase, as similarly described above, while the silicone washer 290 provides a better slow/speed reduction solution at the end of travel. Using the silicone washer 290 at the end of travel instead of silicone gel 291 advantageously avoids the needle hub 280 from simply "crashing" into a pile of silicone gel 291 at the end and provides better speed reduction.

In another embodiment, the silicone washer as the first damping mechanism 290 is disposed at the proximal end of the needle hub 280 and the silicone gel as the second damping mechanism 291 is disposed at the proximal end of the inner diameter of the barrel 272. The silicone washer interacts with the inner diameter of the handle 271 and the barrel 272 to control initial retraction of the needle hub 280 as similarly described above. The silicone gel at the proximal end of the inner diameter of the barrel 272 contacts the needle hub 280 to slow the end of travel in the barrel 272. Such a configuration advantageously provides another way to control the speed damping profile during needle retraction.

In another embodiment, the silicone gel as the second damping mechanism 291 is disposed at the proximal end of the needle hub 280, applied to the spring 82, 182 and disposed at the proximal end of the inner diameter of the barrel 272. The silicone gel at the proximal end of the needle hub 280 contacts the inner diameter of the handle 271 to slow the retraction speed. A similar effect happens with the silicone gel 291 at the proximal end of the inner diameter of the barrel 272 as the needle hub 280 approaches the end of travel in the barrel 272. However, at the proximal end of the inner diameter of the barrel 272, the spring also mixes with the residual silicone gel from the proximal end of the needle hub 280 to provide further damping of the retraction speed. In this manner, the silicone gel 291 advantageously slows retraction of the needle hub 280 at the end to obtain a smoother deceleration and stoppage of the needle hub 280 in the retracted position. Such a configuration advantageously provides another way to control the speed damping profile during needle retraction while only using silicone gel. In another embodiment, access holes 292 are advantageously provided near any one of the proximal end of the spring 82, 182, the proximal end of the needle hub 280 in the first needle position and the proximal end of the inner diameter of the handle 271 and the barrel 272. In this manner, silicone gel 291 can be easily and accurately applied by the user at the desired locations described in the embodiments above.

The foregoing detailed description of the certain exemplary embodiments has been provided for the purpose of explaining the principles of the invention and its practical application, thereby enabling others skilled in the art to understand the invention for various embodiments and with various modifications as are suited to the particular use contemplated. This description is not necessarily intended to be exhaustive or to limit the invention to the precise embodiments disclosed. Any of the embodiments and/or elements disclosed herein may be combined with one another to form various additional embodiments not specifically disclosed, as long as they do not contradict each other. Accordingly, additional embodiments are possible and are intended to be encompassed within this specification and the scope of the invention. The specification describes specific examples to accomplish a more general goal that may be accomplished in another way.

As used in this application, the terms "front," "rear," "upper," "lower," "upwardly," "downwardly," and other orientational descriptors are intended to facilitate the description of the exemplary embodiments of the present invention, and are not intended to limit the structure of the exemplary embodiments of the present invention to any particular position or orientation. Terms of degree, such as "substantially" or "approximately" are understood by those of ordinary skill to refer to reasonable ranges outside of the given value, for example, general tolerances associated with manufacturing, assembly, and use of the described embodiments.

What is claimed is:

1. A catheter assembly comprising:
a catheter carried by a catheter adapter;
a needle having a distal tip and disposed in the catheter such that in a first needle position, the needle extends beyond the catheter;
a damping mechanism fixed adjacent to a proximal end of the needle; and a barrel assembly configured to surround the damping mechanism, the barrel assembly including first and second inner diameters, the first inner diameter is smaller than an outer diameter of the damping mechanism; wherein when the needle is retracted into the barrel assembly away from the first needle position, the needle moves in accordance with a needle retraction speed profile; and the needle retraction speed profile is based on the interaction between the first and second inner diameters of the barrel assembly and the damping mechanism.

2. The catheter assembly of claim 1, wherein a spring clip is disposed in the catheter adapter; and the spring clip cooperates with the needle such that the spring clip is biased on the needle in the first needle position and the spring clip is unbiased and blocks the distal tip of the needle in a second needle position to prevent returning to the first needle position.

3. The catheter assembly of claim 1, wherein the barrel assembly includes a third inner diameter; and the third inner diameter is smaller than the outer diameter of the damping mechanism.

4. The catheter assembly of claim 3, wherein friction between the damping mechanism and the first inner diameter slows a retraction speed of the needle in the barrel assembly, clearance between the damping mechanism and the second inner diameter increases the retraction speed of the needle in the barrel assembly when compared to the retraction speed of the needle at the first inner diameter, and friction between the damping mechanism and the third inner diameter slows the retraction speed of the needle to a resting position at a proximal end of the barrel assembly.

5. The catheter assembly of claim 3, wherein the first and third inner diameters are substantially similar; and the second inner diameter is larger than the first inner diameter and the third inner diameter, respectively.

6. The catheter assembly of claim 1, wherein when the needle is in a second needle position, a clip encloses the distal tip of the needle.

7. The catheter assembly of claim 1, wherein when the needle moves to a third needle position, the needle is retracted into the barrel assembly via spring force from a spring.

8. The catheter assembly of claim 1, wherein the damping mechanism comprises a silicon washer.

9. The catheter assembly of claim 1, wherein a smooth transition is provided between the first and second diameters of the barrel assembly.

10. The catheter assembly of claim 9, wherein the smooth transition provides a gradual change in a retraction speed of the needle.

11. The catheter assembly of claim 1, wherein the second inner diameter is larger than the first inner diameter.

12. The catheter assembly of claim 1, wherein a width of one of the first and second inner diameters of the barrel assembly is adjusted to alter the needle retraction speed profile.

13. The catheter assembly of claim 12, wherein a retraction speed of the needle decreases as the damping mechanism travels through the width of one of the first and second inner diameters of the barrel assembly.

14. The catheter assembly of claim 1, wherein the damping mechanism is directly fixed to the proximal end of the needle.

* * * * *